US009824457B2

(12) United States Patent
Wenzel et al.

(10) Patent No.: US 9,824,457 B2
(45) Date of Patent: Nov. 21, 2017

(54) MODEL-BASED SEGMENTATION OF AN ANATOMICAL STRUCTURE

(71) Applicant: KONINKLIJKE PHILIPS N.V., Eindhoven (NL)

(72) Inventors: Fabian Wenzel, Hamburg (DE); Carsten Meyer, Hamburg (DE); Thomas Heiko Stehle, Hamburg (DE)

(73) Assignee: Koninklijke Philips N.V., Eindhoven (NL)

( * ) Notice: Subject to any disclaimer, the term of this patent is extended or adjusted under 35 U.S.C. 154(b) by 129 days.

(21) Appl. No.: 14/832,029

(22) Filed: Aug. 21, 2015

(65) Prior Publication Data

US 2016/0063726 A1    Mar. 3, 2016

(30) Foreign Application Priority Data

Aug. 28, 2014   (EP) .................................. 14182573

(51) Int. Cl.
*G06K 9/00*   (2006.01)
*G06T 7/12*   (2017.01)
(Continued)

(52) U.S. Cl.
CPC .............. *G06T 7/12* (2017.01); *G06T 7/0012* (2013.01); *G06T 7/13* (2017.01); *G06T 7/149* (2017.01);
(Continued)

(58) Field of Classification Search
CPC ... G06T 7/0089; G06T 7/0083; G06T 7/0085; G06T 2207/30016; G06T 2207/10072; G06T 2207/20004; G06T 2207/10028
See application file for complete search history.

(56) References Cited

U.S. PATENT DOCUMENTS 6,106,466 A  *  8/2000  Sheehan  ..............  A61B 5/1075
                                                                128/916
7,860,283 B2 * 12/2010  Begelman ..........  A61B 5/02007
                                                                345/418
(Continued)

OTHER PUBLICATIONS

Ecabert et al., "Automatic Model-Based Segmentation of the Heart in CT Images," IEEE, pp. 1189-1201, Sep. 2008.*
(Continued)

*Primary Examiner* — Shefali Goradia (57) ABSTRACT

A system (100) and method is provided for performing a model-based segmentation of an anatomical structure in a medical image of a patient. The medical image (022) is accessed. Moreover, model data (162) is provided which defines a deformable model for segmenting the type of anatomical structure. The model-based segmentation of the anatomical structure is performed by adapting the deformable model to the anatomical structure in the medical image using an adaptation technique. In accordance with the present invention, performing the model based segmentation further comprises determining from patient data (042) medical information which is predictive of an appearance of the anatomical structure in the medical image, and adjusting or setting a segmentation parameter based on the medical information so as to adjust the model-based segmentation to said predicted appearance of the anatomical structure in the medical image, the segmentation parameter being a parameter of i) the deformable model or ii) the adaptation technique. Advantageously, the system and method are enabled to better cope with the inter-patient and inter-disease-stage variability in the appearance of anatomical structures.

16 Claims, 4 Drawing Sheets

(51) Int. Cl.
  *G06T 7/00* (2017.01)
  *G06T 7/13* (2017.01)
  *G06T 7/149* (2017.01)
  *G06F 19/00* (2011.01)

(52) U.S. Cl.
  CPC .. *G06F 19/321* (2013.01); *G06T 2207/10028* (2013.01); *G06T 2207/10072* (2013.01); *G06T 2207/20004* (2013.01); *G06T 2207/20116* (2013.01); *G06T 2207/30016* (2013.01)

(56) References Cited

U.S. PATENT DOCUMENTS

| | | | |
|---|---|---|---|
| 8,918,657 B2 * | 12/2014 | Cameron | G06Q 10/04 713/300 |
| 2003/0160786 A1 * | 8/2003 | Johnson | G06T 17/20 345/419 |
| 2006/0115135 A1 | 6/2006 | Dehmeshki et al. | |
| 2007/0276214 A1 | 11/2007 | Dachille et al. | |
| 2011/0160546 A1 | 6/2011 | Madsen | |
| 2013/0325493 A1 | 12/2013 | Wong et al. | |
| 2015/0110369 A1 | 4/2015 | Saalbach et al. | |

OTHER PUBLICATIONS

World Health Organization: Dementia: a public health priority http://www.who.int/mental_health/publications/dementia_report_2012/en/.

Slavin, M.J. et al. "Hippocampal Volume and the Mini-Mental State Examination in the Diagnosis of Amnestic Mild Cognitive Impairment", AJR: 188, May 2007, p. 1404-1410.

Zhuang, A.J. et al. "Skull-stripping magnetic resonance brain images using a model-based level set", Neuroimage, Academic Press, Orlando, FL, vol. 32, No. 1, 2006, pp. 79-92.

Guetat G. et al., "A fast algorithm for body extraction in a CT volumes", Proceedings of SPIE, SPIE—International Society for Optical Engineering, vol. 6144, 2006, pp. 61444C-1.

Martin, S. et al, "Automated segmentation of the prostate in 3D MR images using a probabilistic atlas and a spatially constrained deformable model", Medical Physics, AIP, Melville, NY, vol. 37, No. 4, 2010, pp. 1579-1590.

Baillard, C. et al. "Segmentation of brain 3D MR images using level sets and dense registration", Medical Image Analysis, vol. 5, No. 3, 2001, pp. 185-194.

* cited by examiner

MODEL-BASED SEGMENTATION OF AN ANATOMICAL STRUCTURE

FIELD OF THE INVENTION

The invention relates to a system and a method for performing a model-based segmentation of an anatomical structure in a medical image. The invention further relates to a workstation and imaging apparatus comprising the system and to a computer program product comprising instructions for causing a processor system to perform the method.

BACKGROUND OF THE INVENTION

Robust automatic segmentation of various anatomical structures in a medical image is a key enabler in improving clinical workflows. Here, the term segmentation refers to the identification of the anatomical structure in the medical image by, e.g., delineation of the boundaries of the anatomical structure, by labeling of the voxels enclosed by the boundaries, etc. Once such segmentation has been performed, it is possible to extract clinical parameters such as, in case of, e.g., a cardiac structure, ventricular mass, ejection fraction and wall thickness. Consequently, automatic segmentation can significantly reduce the scan-to-diagnosis time, and thus help clinicians in establishing more efficient patient management.

It is known to segment an anatomical structure in a medical image using a deformable surface model. Such type of segmentation is also referred to as model-based segmentation. The deformable model may be defined by model data. The model data may define a geometry of the anatomical structure, e.g., in the form of a multi-compartmental mesh of triangles. Inter-patient and inter-disease-stage shape variability may be modeled by assigning an affine transformation to each part of such a deformable model. Affine transformations cover translation, rotation, scaling along different coordinate axes and shearing. Moreover, mesh regularity may be maintained by interpolation of the affine transformations at the transitions between different parts of the deformable model.

The applying of a deformable model to the image data of the medical image may involve the use of an adaptation technique, also termed 'mesh adaptation' in case of a mesh-based model. For example, the adaptation technique may comprise optimizing an energy function based on an external energy term which adapts the deformable model to the image data and an internal energy term which maintains a rigidity of the deformable model.

Deformable models of the above type, as well as other types, are known per se, as are adaptation techniques for the applying of such models to a medical image.

For example, a publication titled "*Automatic Model-based Segmentation of the Heart in CT Images*" by O. Ecabert et al., IEEE Transactions on Medical Imaging 2008, 27(9), pp. 1189-1201, describes a model-based approach for the automatic segmentation of the heart (four chambers, myocardium, and great vessels) from three-dimensional (3D) Computed Tomography (CT) images. Here, model adaptation is performed progressively increasing the degrees-of-freedom of the allowed deformations to improve convergence as well as segmentation accuracy. The heart is first localized in the image using a 3D implementation of the generalized Hough transform. Pose misalignment is corrected by matching the model to the image making use of a global similarity transformation. The complex initialization of the multi-compartment mesh is then addressed by assigning an affine transformation to each anatomical region of the model. Finally, a deformable adaptation is performed to accurately match the boundaries of the patient's anatomy.

SUMMARY OF THE INVENTION

A problem of the known deformable models and/or their adaptation techniques is that they are insufficiently able to cope with inter-patient and inter-disease-stage variability in the appearance of anatomical structures across medical images. Here, the term 'appearance' refers to visual aspects such as the shape, size, image contrast, etc., of the anatomical structure being shown in the medical image. Accordingly, after adaptation, the deformable model may insufficiently fit the anatomical structure.

It would be advantageous to have a system or method for performing a model-based segmentation of an anatomical structure in a medical image which is able to better cope with the inter-patient and inter-disease-stage variability in said appearance.

A first aspect of the invention provides a system for performing a model-based segmentation of an anatomical structure in a medical image of a patient, the system comprising:
- an image interface for accessing the medical image;
- a patient data interface for accessing patient data of the patient;
- a data storage comprising model data defining a deformable model for segmenting the type of anatomical structure; and
- a processor configured for performing a model-based segmentation of the anatomical structure by adapting the deformable model to the anatomical structure in the medical image using an adaptation technique;

wherein the processor is further configured for:
- determining, from the patient data, medical information which is predictive of an appearance of the anatomical structure in the medical image; and
- adjusting or setting a segmentation parameter based on the medical information so as to adjust the model-based segmentation to said predicted appearance of the anatomical structure in the medical image, the segmentation parameter being a parameter of i) the deformable model or ii) the adaptation technique.

A further aspect of the invention provides a workstation or imaging apparatus comprising the system.

A further aspect of the invention provides a method for performing a model-based segmentation of an anatomical structure in a medical image of a patient, the method comprising:
- accessing the medical image;
- accessing patient data of the patient;
- providing model data defining a deformable model for segmenting a type of anatomical structure;
- performing a model-based segmentation of the anatomical structure by adapting the deformable model to the anatomical structure in the medical image using an adaptation technique;

wherein the performing of the model-based segmentation comprises:
- determining, from the patient data, medical information of the patient which is predictive of an appearance of the anatomical structure in the medical image; and
- adjusting or setting a segmentation parameter based on the medical information so as to adjust the model-based segmentation to said predicted appearance of the anatomical structure in the medical image, the segmentation parameter being a parameter of i) the deformable model or ii) the adaptation technique.

A further aspect of the invention provides a computer program product comprising instructions for causing a processor system to perform the method.

The above measures involve obtaining a medical image of a patient. The medical image shows an anatomical structure of the patient such as an organ, a part of the organ, etc. Such medical images may be obtained using various imaging modalities such as, e.g., CT, Magnetic Resonance (MR) imaging, etc. Furthermore, model data is provided which defines a deformable model for segmenting the type of anatomical structure as shown in the medical image. For example, the deformable model may be arranged for segmenting the human brain or a part thereof. The deformable model may thus initially be a non-patient specific deformable model. The model data is comprised on a data storage such as semiconductor memory, a magnetic or optical disk, etc. Furthermore, a processor is provided for performing a model-based segmentation of the anatomical structure, namely by applying the deformable model to image data of the medical image. For that purpose, the processor uses an adaptation technique. Such an adaptation technique may be represented by, e.g., data defining a plurality of operations. It is noted that the functionality described in this paragraph is known per se from the field of model-based segmentation of anatomical structures.

A patient data interface is provided for accessing patient data of the patient. Here, the term 'patient data' refers to patient-specific medical data, e.g., by being specific to the patient itself or to a limited group of patients of which the patient is a part of. For example, the patient data may be constituted by an electronic health record of the patient.

The processor is configured for determining medical information from the patient data which is predictive of an appearance of the anatomical structure in the medical image. As such, the processor obtains medical information which has a predictive quality for a particular kind of appearance of the anatomical structure. The predictive quality may be due to the existence of a correlation or causality between the medical information and the particular kind of appearance of the anatomical structure. A non-limiting example is that Alzheimer's disease may be associated with atrophy of the hippocampus. Accordingly, medical information in the patient data which denotes the patient suffering from Alzheimer's may be predictive of the hippocampus having a decreased size in the medical image.

The processor is further configured for adjusting or setting a segmentation parameter based on the medical information. The segmentation parameter is a parameter which is used in the model-based segmentation, namely a parameter of the deformable model or the adaptation technique. By doing so, the processor adjusts the model-based segmentation to the predicted appearance of the anatomical structure in the medical image. In this context, the term 'adjusting' refers to a biasing of the model-based segmentation towards the predicted appearance of the anatomical structure in the medical image. Accordingly, by adjusting or setting the segmentation parameter based on the medical information, the model-based segmentation may be suitably initialized or, during adaptation, suitably adjusted.

The above measures address one of the fundamental challenges of model-based segmentation, namely the high degree of variability in the appearance of anatomical structures across several patients or clinical phases of a particular patient. Although measures exist to address such variability, e.g., by assigning an affine transformation to each part of such a deformable model so as to model this variability, further improvements are desirable. The inventors have recognized that there typically exists patient data which comprises medical information that has a predictive quality on the appearance of an anatomical structure in a particular medical image, and that such patient data may be used to improve the model-based segmentation. By providing the segmentation system with a patient data interface to the patient data of the particular patient associated with the medical image, the segmentation system is provided with such medical information. Accordingly, the segmentation system can optimize the model-based segmentation for the particular medical image using the medical information, namely by adjusting or setting one or more parameters of the model-based segmentation so as to obtain a better fit to the anatomical structure in the medical image. Advantageously, the segmentation system is enabled to better cope with the inter-patient and inter-disease-stage variability in the appearance of anatomical structures.

Optionally, the segmentation parameter has a pre-initialization value for use in adapting the deformable model to a reference appearance of the anatomical structure, and the processor is configured for:
  based on the medical information, determining a deviation of the predicted appearance of the anatomical structure from the reference appearance; and
  adjusting the segmentation parameter to accommodate said deviation.

The segmentation parameter may have a value which has been preset for a reference appearance of the anatomical structure. The processor may adjust the value of the segmentation parameter to compensate for the deviation between this reference appearance and the predicted appearance. Accordingly, the segmentation parameter is better suited for adapting the deformable model to the predicted appearance of the anatomical structure.

Optionally, the reference appearance is an inter-patient mean appearance of the anatomical structure. The deformable model and/or the adaptation technique may be pre-configured for an inter-patient mean appearance of the anatomical structure. Here, the term 'inter-patient mean appearance' refers to an appearance representing a statistical mean across a group of patient, e.g., a norm appearance. The segmentation parameter may be preset for this mean appearance. The processor may adjust the value of the segmentation parameter to compensate for the deviation of the anatomical structure in the medical image from this mean appearance in view of the predicted appearance of the anatomical structure.

Optionally, the segmentation parameter determines at least in part a geometric shape of the deformable model. Accordingly, by adjusting or setting the segmentation parameter, at least a part of the geometric shape of the deformable model is adjusted or set. It is noted that, additionally or alternatively, the segmentation parameter may adjust or set an appearance feature or other (multi-modal) derived quantity of the model-based segmentation, such as a fiber orientation parameter. This may apply in case the model-based segmentation makes use of such appearance features or other (multi-modal) derived quantities.

Optionally, the segmentation parameter determines a degree of allowable shape deformation of the deformable model during the adapting of the deformable model. Here, the term 'allowable shape deformation' refers to constraints in the shape deformation of the deformable model, as established by data of the deformable model and/or the adaptation technique. Such constraints may be defined by, e.g., parameters of energy functions, weighting functions, etc. Accordingly, by adjusting or setting the segmentation parameter, the allowable shape deformation of the deformable model is adjusted or set.

Optionally, the medical information is indicative of an anatomical part of the anatomical structure having an abnormal shape or size, and the processor is configured for adjusting or setting the segmentation parameter to allow or restrict the shape deformation of a model part of the deformable model which corresponds to said anatomical part. The medical information may be indicative of a local deformation of the anatomical structure, in that an anatomical part of the anatomical structure may have an abnormal shape or size. The segmentation parameter is adjusted or set to determine the degree of allowable shape deformation of a corresponding model part of the deformable model. Advantageously, a higher degree of shape deformation may be locally allowed so as to enable the deformable model to fit anatomical parts of the anatomical structure having abnormal shapes or sizes.

Optionally, the medical information is predictive of an image contrast at a boundary of the anatomical structure in the medical image, the segmentation parameter is for use in edge detection, and the processor is configured for adjusting or setting the segmentation parameter to optimize the edge detection for said predicted image contrast. The adaptation technique may be based on edge detection. The image contrast, either locally or globally, may have an effect on edge detection in that, for a different image contrast, different parameters may be needed to optimally detect an edge in the medical image. By adjusting or setting the segmentation parameter based on the predicted image contrast, the edge detection is optimized so as to take into account said image contrast. Advantageously, a more accurate edge detection is obtained, resulting in an improved fit of the deformable model. It is noted that, additionally or alternatively, the medical information may be predictive of any other type of image-related quantity, and the segmentation parameter may be used for determining a target position for the model-based segmentation based on the image-related quantity.

Optionally, the medical information comprises at least one of: an age, a gender, a disease type, a disease progression state, of the patient. Such types of medical information has been found to correlate well, or have a causal relation, with an appearance of an anatomical structure in a medical image of the patient. However, this is not a limitation, in that other types of medical information may be used as well.

Optionally, the adaptation technique is represented by data defining a plurality of operations, and the segmentation parameter defines an order or a sub-selection of the plurality of operations to be performed by the processor. Accordingly, the predicted appearance of the anatomical structure is used to adjust or set the order, or determine a sub-selection, of the operations to be performed by the processor. For example, depending on the predicted appearance, pre-processing steps may be selected or rather omitted from selection. Another example is that the deformable model may comprise a plurality of model parts corresponding to respective anatomical parts of anatomical structure, and at least part of the plurality of operations may be for the adapting of respective ones of the plurality of model parts. Accordingly, the predicted appearance of the anatomical structure may be used to adjust or set the order, or determine a sub-section, of the model parts to be fitted.

Optionally, the patient data is constituted by an electronic health record of the patient. An electronic health record is well-suited for obtaining medical information that is predictive of an appearance of the anatomical structure in the medical image. For example, the electronic health record may indicate a reason for the medical image being acquired, with the reason constituting medical information that may be used to predict said appearance.

Optionally, the medical image is a DICOM formatted image, and the patient data is constituted by DICOM metadata of the DICOM formatted image. The inventors have recognized that DICOM metadata, e.g., as included in a header of a DICOM formatted image, may comprise medical information which is also suitable for predicting an appearance of the anatomical structure comprised in the DICOM formatted image.

In accordance with the above, a system and method may be provided for performing a model-based segmentation of an anatomical structure in a medical image of a patient. The medical image may be accessed. Moreover, model data may be provided which defines a deformable model for segmenting the type of anatomical structure. The model-based segmentation of the anatomical structure may be performed by adapting the deformable model to the anatomical structure in the medical image using an adaptation technique. Performing the model based segmentation may further comprise determining from patient data medical information which is predictive of an appearance of the anatomical structure in the medical image, and adjusting or setting a segmentation parameter based on the medical information so as to adjust the model-based segmentation to said predicted appearance of the anatomical structure in the medical image, the segmentation parameter being a parameter of i) the deformable model or ii) the adaptation technique. Advantageously, the system and method may better cope with inter-patient and inter-disease-stage variability in the appearance of anatomical structures.

It will be appreciated by those skilled in the art that two or more of the above-mentioned embodiments, implementations, and/or aspects of the invention may be combined in any way deemed useful.

Modifications and variations of the imaging apparatus, the workstation, the method, and/or the computer program product, which correspond to the described modifications and variations of the system, can be carried out by a person skilled in the art on the basis of the present description.

A person skilled in the art will appreciate that the method may be applied to multi-dimensional image data, e.g. to two-dimensional (2D), three-dimensional (3D) or four-dimensional (4D) images, acquired by various acquisition modalities such as, but not limited to, standard X-ray Imaging, Computed Tomography (CT), Magnetic Resonance Imaging (MRI). Ultrasound (US), Positron Emission Tomography (PET), Single Photon Emission Computed Tomography (SPECT), and Nuclear Medicine (NM).

The invention is defined in the independent claims. Advantageous embodiments are defined in the dependent claims.

BRIEF DESCRIPTION OF THE DRAWINGS

These and other aspects of the invention are apparent from and will be elucidated with reference to the embodiments described hereinafter. In the drawings.

It should be noted that items which have the same reference numbers in different Figures, have the same structural features and the same functions, or are the same signals. Where the function and/or structure of such an item has been explained, there is no necessity for repeated explanation thereof in the detailed description.

LIST OF REFERENCE NUMBERS

The following list of reference numbers is provided for facilitating the interpretation of the drawings and shall not be construed as limiting the claims.
020 image repository
022, 022A, 022B medical image
024 image data of DICOM formatted medical image
040 patient data repository
042 patient data
100 system for performing model-based segmentation
120 image interface
140 patient data interface
160 data storage
162 model data defining deformable model
180 processor
200 method for performing model-based segmentation
210 accessing medical image
220 accessing patient data
230 providing model data defining deformable model
240 determining medical information predictive of appearance
245 determining deviation from the reference appearance
250 adjusting or setting segmentation parameter
260 adapting deformable model
270 non-transitory data representing instructions
280 computer readable medium
300, 302 deformable model
310 reference appearance of anatomical structure
320, 322 deformable model adjusted based on medical information
330 predicted appearance of anatomical structure
340, 342 ventricular volume
400 medical information, age of the patient
410 medical information, gender of the patient
420 medical information, disease type of the patient
430 medical information, disease progression state of the patient

DETAILED DESCRIPTION OF EMBODIMENTS

Figure 1:
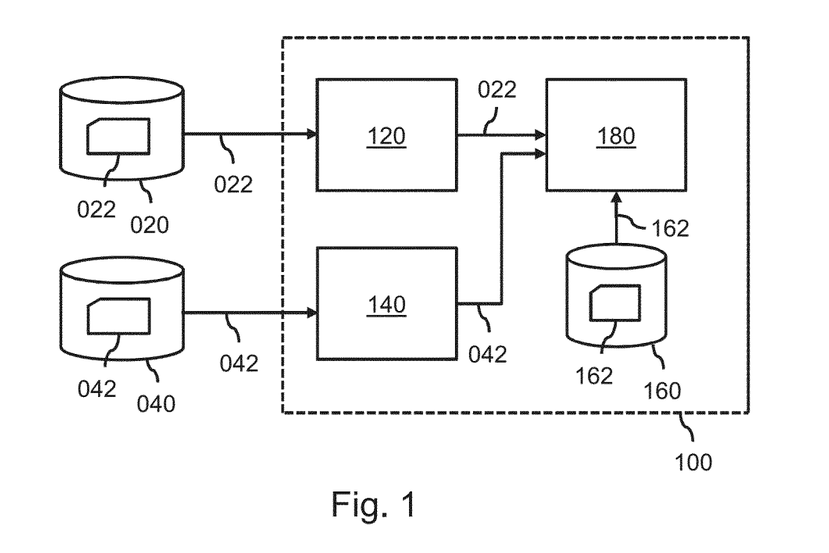
FIG. 1 shows a system for performing a model-based segmentation of an anatomical structure in a medical image in which the model-based segmentation is adjusted to the predicted appearance of the anatomical structure in the medical image.

FIG. 1 shows a system 100 for performing a model-based segmentation of an anatomical structure in a medical image of a patient. The system 100 comprises an image interface 120 for accessing the medical image 022. In the example of FIG. 1, the image interface 120 is shown to be connected to an image repository 020. For example, the image repository 020 may be constituted or be part of a Picture Archiving and Communication System (PACS) of a Hospital Information System (HIS) to which the system 100 may be connected or comprised in. Accordingly, the system 100 may obtain access to the medical image 022. In general, the image interface 120 may take various forms, such as a network interface to a local or wide area network, a storage interface to an internal or external storage, etc. Moreover, it is noted that the medical image 022 may be represented by image data, and that the system 100 may access the medical image 022 by obtaining access to its image data. Accordingly, throughout this text and where appropriate, a reference to the medical image 022 is to be understood as referring to the image data representing the medical image 022.

The system 100 further comprises a data storage 160 comprising model data 162 defining a deformable model for segmenting the type of anatomical structure shown in the medical image 022. For example, the model data 162 may define a mesh of triangles. The data storage 160 is shown to be an internal component of the system 100, and may be constituted by, e.g., a disk-based data storage such as a hard disk, a semiconductor-based data storage such as a ROM or RAM memory, a removable storage medium inserted into a storage medium reader, etc. It is noted that the data storage 160 may also be separately provided, e.g., in the form of a removable storage medium comprising the model data 162.

The system 100 further comprises a processor 180 configured for performing a model-based segmentation of the anatomical structure by adapting the deformable model to the anatomical structure in the medical image 022 using an adaptation technique. For that purpose, the processor 180 is shown to access the medical image 022 via the image interface 120 and obtain the model data 162 from the data storage 160. The system 100 further comprises a patient data interface 140 for accessing patient data 042 of the patient. In the example of FIG. 1, the patient interface 140 is shown to be connected to a patient data repository 040. An example of a patient data repository is an Electronic Health Record (EHR) repository. Another term for the EHR of a patient is Electronic Patient Record (EPR). The EHR repository may be part of a HIS to which the system 100 may be connected or comprised in. However, this is not a limitation, in that use may also be made of patient data other than an electronic health or patient record, as will be elucidated further. In general, the patient data interface 120 may take various forms, such as a network interface to a local or wide area network, a storage interface to an internal or external storage, etc.

The processor 180 is configured for, during operation of the system 100, performing the following operations. The processor 180 determines from the patient data 042 medical information which is predictive of an appearance of the anatomical structure in the medical image 022. Having determined the medical information, the processor 180 then adjusts or sets a segmentation parameter based on the medical information so as to adjust the model-based segmentation to said predicted appearance of the anatomical structure in the medical image. The segmentation parameter is a parameter of i) the deformable model or ii) the adaptation technique. Furthermore, although not shown in FIG. 1, the processor 180 may output a result of the model-based segmentation, e.g., the adapted model. However, the result of the model-based segmentation may also be further used internally within the system.

It is noted that various operations of the system 100, and in particular those off the processor 180, will be explained in more detail with reference to FIGS. 4-6.

The system 100 may be embodied as, or in, a single device or apparatus, such as a workstation or imaging apparatus. The device or apparatus may comprise one or more microprocessors which execute appropriate software. The software may have been downloaded and/or stored in a corresponding memory, e.g., a volatile memory such as RAM or a non-volatile memory such as Flash. Alternatively, the functional units of the system may be implemented in the device or apparatus in the form of programmable logic, e.g., as a Field-Programmable Gate Array (FPGA). In general, each functional unit of the system may be implemented in the form of a circuit. It is noted that the system 100 may also be implemented in a distributed manner, e.g., involving different devices or apparatuses. For example, the distribution may be in accordance with a client-server model.

Figure 2:
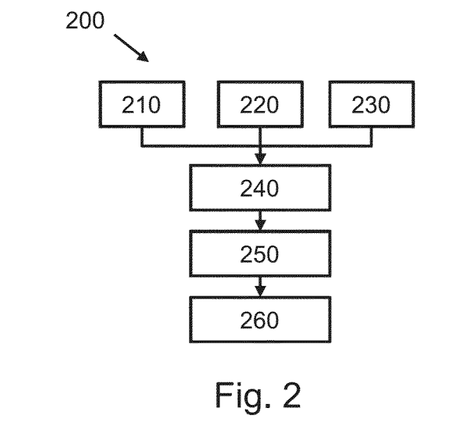
FIG. 2 shows a method for performing the model-based segmentation.

FIG. 2 shows a method 200 for performing a model-based segmentation of an anatomical structure in a medical image of a patient. The method 200 may correspond to an operation of the system 100 of FIG. 1. However, this is not a limitation, in that the method 200 may also be performed using one or more different devices or apparatuses.

The method 200 comprises, in an operation titled "ACCESSING MEDICAL IMAGE", accessing 210 the medical image. The method 200 further comprises, in an operation titled "ACCESSING PATIENT DATA", accessing 220 patient data of the patient. The method 200 further comprises, in an operation titled "PROVIDING MODEL DATA DEFINING DEFORMABLE MODEL", providing 230 model data defining a deformable model for segmenting a type of anatomical structure. The method 200 further comprises, in an operation titled "ADAPTING DEFORMABLE MODEL", performing a model-based segmentation of the anatomical structure by adapting 260 the deformable model to the anatomical structure in the medical image using an adaptation technique. Here, the performing of the model-based segmentation comprises, in an operation of the method 200 titled "DETERMINING MEDICAL INFORMATION PREDICTIVE OF APPEARANCE", determining 240 from the patient data medical information which is predictive of an appearance of the anatomical structure in the medical image, and in an operation of the method 200 titled "ADJUSTING OR SETTING SEGMENTATION PARAMETER BASED ON PREDICTED APPEARANCE", adjusting or setting 250 a segmentation parameter based on the medical information so as to adjust the model-based segmentation to said predicted appearance of the anatomical structure in the medical image, the segmentation parameter being a parameter of i) the deformable model or ii) the adaptation technique.

It will be appreciated that the above operation may be performed in any suitable order, e.g., consecutively, simultaneously, or a combination thereof, subject to, where applicable, a particular order being necessitated, e.g., by input/output relations.

Figure 3:
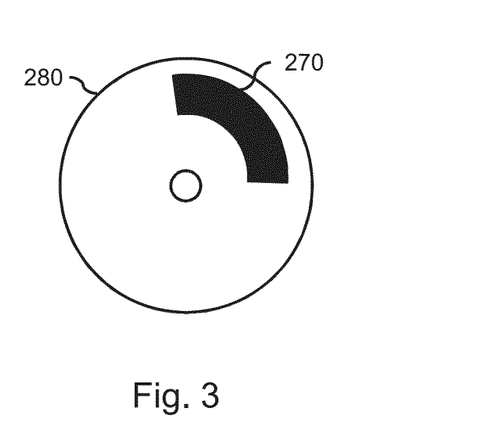
FIG. 3 shows a computer program product for carrying out the method.

The method 200 may be implemented on a computer as a computer implemented method, as dedicated hardware, or as a combination of both. As also illustrated in FIG. 3, instructions for the computer, e.g., executable code, may be stored on a computer readable medium 280, e.g., in the form of a series 270 of machine readable physical marks and/or as a series of elements having different electrical, e.g., magnetic, or optical properties or values. The executable code may be stored in a transitory or non-transitory manner. Examples of computer readable mediums include memory devices, optical storage devices 280, integrated circuits, servers, online software, etc. FIG. 3 shows an optical disc.

The operation of the system of FIG. 1 and the method of FIG. 2, including various optional aspects thereof, may be explained in more detail as follows.

Figure 4:
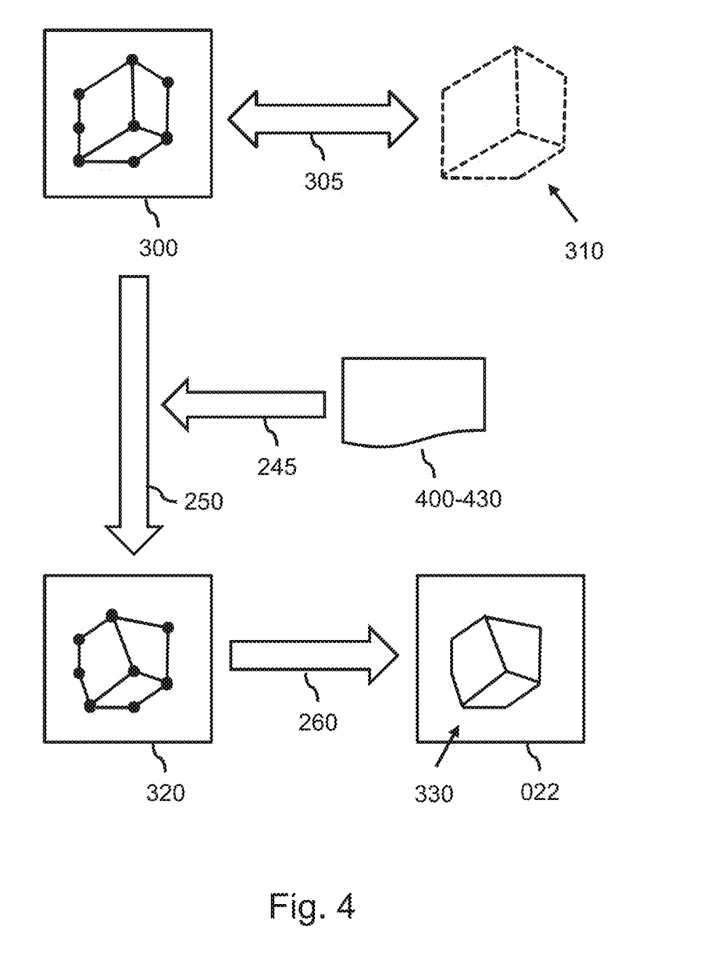
FIG. 4 schematically illustrates the deformable model being associated with a reference appearance of the anatomical structure, and the segmentation parameter being adjusted to accommodate a deviation existing between the predicted appearance of the anatomical structure in the medical image and the reference appearance.

FIG. 4 schematically illustrates the model-based segmentation being adjusted to the predicted appearance of the anatomical structure in the medical image. In the example of FIG. 4, the deformable model 300 is arranged for matching a reference appearance 310 of the anatomical structure. This matching is shown schematically in FIG. 4 by a double-headed arrow 305. Moreover, for case of illustration, the anatomical structure is shown here as a fictitious structure. The deformable model 300 may be arranged for matching this reference appearance by one or more segmentation parameters having a pre-initialization value for use in adapting the deformable model 300 to this reference appearance 310. For example, the value of the segmentation parameter may be selected to match an 'average' appearance of the anatomical structure, e.g., an inter-patient mean appearance 310. A specific example may be that the segmentation parameter has a value which is used as a threshold value in edge detection, with the value being selected to fit the image contrast at a boundary of the anatomical structure in a 'typical' medical image of said anatomical structure. There may, however, be a deviation between this reference appearance and the actual appearance of the anatomical structure in the medical image 022. Causes of this deviation may include inter-patient or inter-disease-stage variability, a disease, etc. To better account for this deviation, and thus to obtain a better segmentation, the processor may be configured for, based on the medical information 400-430, determining 245 a deviation of the predicted appearance 330 of the anatomical structure from the reference appearance, and adjusting 250 the segmentation parameter to accommodate said deviation so as to adjust the deformable model. Accordingly, the deformable model 320 after initialization may be applied 260 to the medical image 022 to obtain a better fit to the actual appearance of the anatomical structure.

Figure 5A:
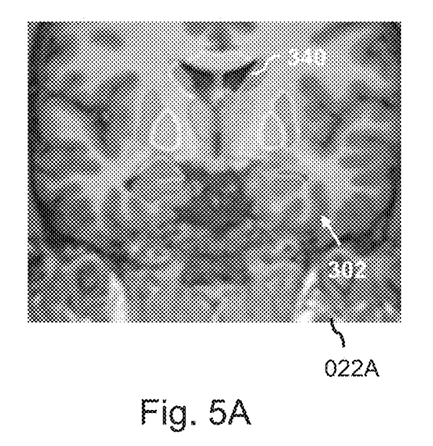
FIG. 5A shows a brain image of a patient not suffering from Alzheimer's disease, with parts of the brain having been segmented using a deformable model.
Figure 5B:
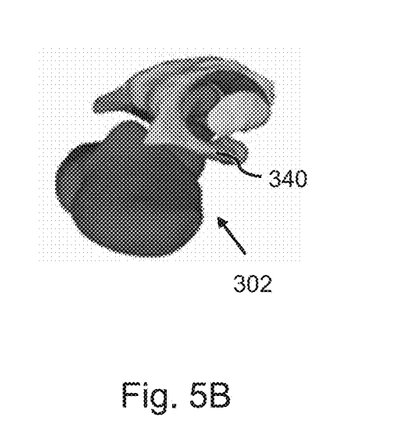
FIG. 5B shows the deformable model of FIG. 5A.
Figure 6A:
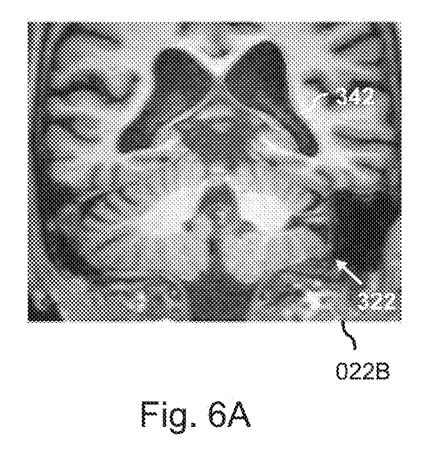
FIG. 6A shows a brain image of a patient suffering from Alzheimer's disease, with parts of the brain having been segmented using a deformable model.
Figure 6B:
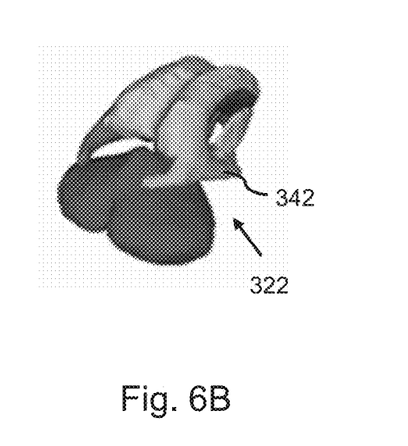
FIG. 6B shows the deformable model of FIG. 6A.

FIGS. 5A-6B provide a real-life example of the schematic illustration of FIG. 4. Here, FIG. 5A shows a brain image 022A of a patient not suffering from Alzheimer's disease, i.e., a normal subject, with parts of the brain having been segmented using a deformable model 302. These parts include a ventricular volume 340. FIG. 5B shows the deformable model 302 of FIG. 5A in isolation. FIG. 6A shows a brain image 022B of a patient suffering from Alzheimer's disease, with parts of the brain having been segmented using a same type of deformable model 322. FIG. 6B shows the deformable model 322 of FIG. 6A in isolation. As can be seen, the deformable model 322 differs from that of FIG. 5B in shape and size so as to provide a better fit with the actual brain shown in the medical image 022B. Here, use is made of the medical fact that further progression in Alzheimer's correlates with an increase in ventricular space of the temporal lobes, leading to a larger ventricular area that has a clear edge contrast between brain liquid (CSF) and White Matter (WM). Accordingly, the shape features of the deformable model 322 and/or the adaptation technique used for its adaptation may be adjusted or set such that shape variation which drives the internal energy components of model-based segmentation is adjusted to the patient suffering from Alzheimer's.

Figure 7:
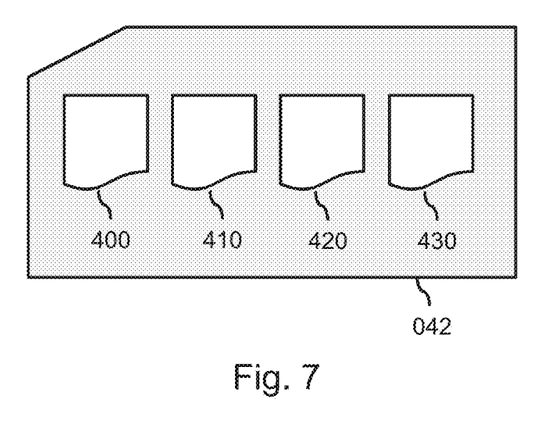
FIG. 7 shows the patient data comprising various medical information.

FIG. 7 shows the patient data 042 comprising various medical information. In this example, the patient data 042 may be constituted by an EHR of the patient. For example, the EHR 042 may comprise, or be indicative of, an age 400 of the patient, a gender 410 of the patient, a disease type 420 of the patient and/or a disease progressions state 430 of the patient. It will be appreciated that the above list of medical information serves as an example rather than constitutes a limitation, as in general, medical information may be predictive of an appearance of the anatomical structure in a medical image of a patient in various ways.

Similarly, there exists various ways of initializing the model-based segmentation to said predicted appearance of the anatomical structure. For example, as was illustrated in FIG. 4, the segmentation parameter may determine at least in part a geometric shape of the deformable model. As such, the geometric shape of the deformable model may be adjusted to the predicted appearance of the anatomical structure. A specific example is that a segmentation parameter may be adjusted or set which determines a degree of allowable shape deformation of the deformable model during the adapting of the deformable model. Accordingly, in case the medical information 400-300 is indicative of an anatomical part of the anatomical structure having an abnormal shape or size, the segmentation parameter may be adjusted or set to allow or restrict the shape deformation of a model part of the deformable model which corresponds to this anatomical part. Another example is that when the medical information is predictive of an image contrast at a boundary of the anatomical structure in the medical image, a segmentation parameter which is used in an edge detection operation may be adjusted or set to optimize the edge detection for said predicted image contrast.

The following are specific examples indicating how medical information may be predictive of the appearance of the anatomical structure in the medical image, and how the model-based segmentation may be adjusted to said predicted appearance. Here, the examples are medical application of brain segmentation. It will be appreciated, however, that similar examples exist in various other medical applications, such as heart segmentation.

The medical information may comprise or be indicative of an age of the patient. Increased patient age typically correlates with an increase in ventricular volume, e.g., the size of the ventricles, in particular towards the occipital horns of the lateral ventricles. Accordingly, a segmentation parameter may be adjusted or set which allows a ventricle model to deform more towards the back of the brain in case the medical image is of an older patient. Likewise, in case the medical image is of a younger patient, the segmentation parameter be adjusted or set to disallow or further restrict such deformation.

Another example of the appearance of the anatomical structure correlating with the age of the patient is the following. In this example, the adaptation technique may be represented by data defining a plurality of operations, and the segmentation parameter may define an order or a subselection of the plurality of operations to be performed by the processor. For example, the operations may relate to the segmentation of respective parts or regions of the anatomical structure. Accordingly, since the ventricles of an older patient are typically expected to appear more dominantly in the medical image, the adaptation technique may, in the order of regions to be adapted, first select the regions of the ventricles so as to increase the robustness of the segmentation in older patients. On the other hand, in younger patients, the ventricles typically appear to be smaller and, in some cases, difficult to delineate. Accordingly, the adaptation technique may refrain from selecting the ventricles first in the order of regions to be adapted as they do not provide robust image features.

Increasing patient age also correlates with an increased number of lesions in the left and right putamen, making the surface border between the putamen and the adjacent structures more difficult to delineate. Accordingly, image characteristics of the putamen, such as the typical distribution of image intensities inside/outside the putamen, may vary with age. Accordingly, image features used in the model-based segmentation be adapted for each representative age range such that a more robust model-based segmentation is obtained, and/or the adaptation order of the model-based segmentation may be adjusted or set such that the putamen is not selected first in the order of regions to be adapted during segmentation, and/or derivations from shape may be penalized more in older subjects such that the likelihood of adapting to incorrect edges which may be caused by lesions in the putamen is decreased. Increasing patient age also correlates with a decrease in Grey Matter (GM)/White Matter (WM) contrast. Accordingly, the edge features of the deformable model and/or the segmentation technique may be adjusted or set such that they are more specific in contrast. Increasing patient age also correlates with an increase in the occurrence of WM Lesions (WML), which often can be found near the ventricles. Accordingly, a different set of edge detection features may be used which favor segmentation robustness over accuracy.

Additionally or alternatively, the medical information may comprise or be indicative of a disease type and a disease progression state of a disease such as, e.g., Alzheimer's. Further progression in Alzheimer's correlates with abnormal deformation of the hippocampus. Accordingly, a segmentation parameter may be adjusted or set to allow or restrict the shape deformation of a corresponding part of the deformable model so as to better fit such a deformation of the hippocampus. Another example is that vascular dementia correlates with an increase in the occurrences of white matter lesions and other changes in contrast. As such, edge features may be adjusted to take the contrast changes into account.

Figure 8:
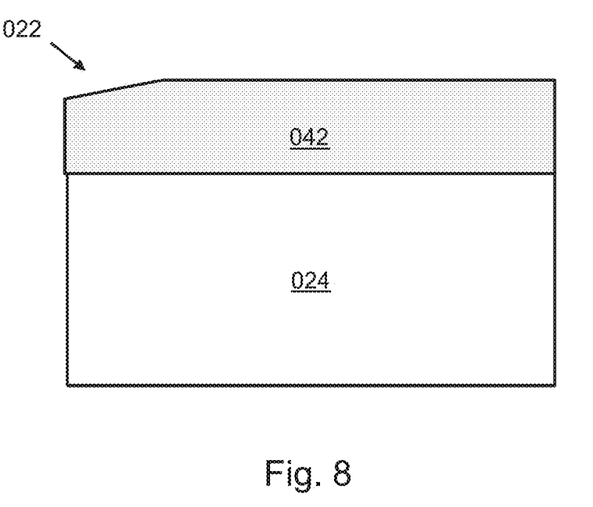
FIG. 8 shows the medical image being a DICOM formatted image, and the patient data being constituted by DICOM metadata of the DICOM formatted image.

FIG. 8 shows the medical image being a DICOM formatted image comprising image data 024 and metadata 042, with the patient data 042 being constituted by DICOM metadata of the DICOM formatted image. As such, the processor may determine the medical information using one or more DICOM attributes such as, e.g., Patient's Age, Patient's Sex. Admitting Diagnoses Description, Interpretation Diagnosis Description, etc.

It will be appreciated that the adjusting or setting of a segmentation parameter based on the medical information may be performed in various ways. For example, a rule-based decision table may be used linking medical information items to segmentation parameters and their values and/or desired adjustments. The typical shape variability in a specific group may be modelled by a principal component analysis of a given reference set, resulting in Eigen-modes which are used in the model-based segmentation to guide the allowed deformations of the deformable model. For example, if medical information in the EHR is categorical, e.g., disease state, gender, etc., then these Eigen-modes may be stored per category. If medical information in the EHR is continuous. e.g. age, modified mean-squared-error, etc., then a linear model of Eigen-modes may be computed, or a non-linear regression technique may be used for modeling. As such, the possible range of typical shape variability may be modeled and linked to an adjustment or setting of one or more segmentation parameters. Moreover, edge detection features may be selected and/or adjusted based on the medical information from the EHR. Here, a look-up table may be used for categorical medical information, a linear model, for continuous medical information, etc.

It will be appreciated that the invention also applies to computer programs, particularly computer programs on or in a carrier, adapted to put the invention into practice. The program may be in the form of a source code, an object code, a code intermediate source and an object code such as in a partially compiled form, or in any other form suitable for use in the implementation of the method according to the invention. It will also be appreciated that such a program may have many different architectural designs. For example, a program code implementing the functionality of the method or system according to the invention may be sub-divided into one or more sub-routines. Many different ways of distributing the functionality among these sub-routines will be apparent to the skilled person. The sub-routines may be stored together in one executable file to form a self-contained program. Such an executable file may comprise computer-executable instructions, for example, processor instructions and/or interpreter instructions (e.g. Java interpreter instructions). Alternatively, one or more or all of the sub-routines may be stored in at least one external library file and linked with a main program either statically or dynamically, e.g. at run-time. The main program contains at least one call to at least one of the sub-routines. The sub-routines may also comprise function calls to each other. An embodiment relating to a computer program product comprises computer-executable instructions corresponding to each processing stage of at least one of the methods set forth herein. These instructions may be sub-divided into sub-routines and/or stored in one or more files that may be linked statically or dynamically. Another embodiment relating to a computer program product comprises computer-executable instructions corresponding to each means of at least one of the systems and/or products set forth herein. These instructions may be sub-divided into sub-routines and/or stored in one or more files that may be linked statically or dynamically.

The carrier of a computer program may be any entity or device capable of carrying the program. For example, the carrier may include a data storage, such as a ROM, for example, a CD ROM or a semiconductor ROM, or a magnetic recording medium, for example, a hard disk. Furthermore, the carrier may be a transmissible carrier such as an electric or optical signal, which may be conveyed via electric or optical cable or by radio or other means. When the program is embodied in such a signal, the carrier may be constituted by such a cable or other device or means. Alternatively, the carrier may be an integrated circuit in which the program is embedded, the integrated circuit being adapted to perform, or used in the performance of, the relevant method.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or stages other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. A system for performing a model-based segmentation of an anatomical structure in a medical image of a patient, the system comprising:
an image interface for accessing the medical image;
a patient data interface for accessing patient data of the patient;
a data storage comprising model data that defines a deformable model for segmenting the type of anatomical structure; and
a processor that:
determines, from the patient data, medical information that is separate and distinct from the medical image;
provides a predicted appearance of the anatomical structure of the patient in the medical image based on the medical information; and
adjusts or sets a segmentation parameter based on the medical information, and
performs a model-based segmentation of the anatomic structure in the medical image based on the deformable model and the segmentation parameter so as to adjust the model-based segmentation to be consistent with the predicted appearance of the anatomical structure in the medical image, the segmentation parameter being a parameter of at least one of the deformable model and the adaptation technique.

2. The system according to claim 1, wherein the segmentation parameter has a pre-initialization value for use in adapting the deformable model to a reference appearance of the anatomical structure, and wherein the processor:
determines, based on the medical information, a deviation of the predicted appearance of the anatomical structure from the reference appearance; and
adjusts the segmentation parameter to accommodate the deviation.

3. The system according to claim 2, wherein the reference appearance is an inter-patient mean appearance of the anatomical structure.

4. The system according to any one of claims 1 to 3, wherein the segmentation parameter determines, at least in part, a geometric shape of the deformable model.

5. The system according to claim 1, wherein the segmentation parameter determines a degree of allowable shape deformation of the deformable model during the adapting of the deformable model.

6. The system according to claim 5, wherein the medical information is indicative of an anatomical part of the anatomical structure having an abnormal shape or size, and wherein the processor is configured for adjusting or setting the segmentation parameter to allow or restrict the shape deformation of a model part of the deformable model that corresponds to the anatomical part.

7. The system according to any one of claims 1 to 3, wherein the medical information is predictive of an image contrast at a boundary of the anatomical structure in the medical image, wherein the segmentation parameter is for use in edge detection, and wherein the processor adjusts or sets the segmentation parameter to optimize the edge detection for the predicted image contrast.

8. The system according to claim 1, wherein the medical information comprises at least one of: an age, a gender, a disease type, a disease progression state, of the patient.

9. The system according to claim 1, wherein the adaptation technique is represented by data defining a plurality of operations, and wherein the segmentation parameter defines an order or a sub-selection of the plurality of operations to be performed by the processor.

10. The system according to claim 9, wherein the deformable model comprises a plurality of model parts corresponding to respective anatomical parts of anatomical structure, and wherein at least part of the plurality of operations are for the adapting of respective ones of the plurality of model parts.

11. The system according to claim 10, wherein the patient data is constituted by an electronic health record of the patient.

12. The system according to claim 1, wherein the medical image is a DICOM (Digital Imaging and Communications in Medicine) formatted image, and wherein the patient data is constituted by DICOM metadata of the DICOM formatted image.

13. Workstation or imaging apparatus comprising the system according to claim 1.

14. A method for performing a model-based segmentation of an anatomical structure in a medical image of a patient, the method comprising:
  accessing the medical image;
  accessing patient data of the patient;
  providing model data defining a deformable model for segmenting a type of anatomical structure;
  performing a model-based segmentation of the anatomical structure by adapting the deformable model to the anatomical structure in the medical image using an adaptation technique;
  wherein the performing of the model-based segmentation comprises:
    determining from the patient data medical information that is separate and distinct from the medical image,
    determining a predicted appearance of the anatomical structure in the medical image based on the medical information; and
    adjusting or setting a segmentation parameter based on the medical information so as to adjust the model-based segmentation to be consistent with the predicted appearance of the anatomical structure in the medical image, the segmentation parameter being a parameter of at least one of the deformable model and the adaptation technique.

15. A non-transitory computer-readable medium that includes a program that, when executed by a processor, causes the processor to:
  access a medical image of a patient;
  access patient data of the patient;
  access model data defining a deformable model for segmenting a type of anatomical structure;
  perform a model-based segmentation of the anatomical structure by adapting the deformable model to the anatomical structure in the medical image using an adaptation technique;
  wherein the processor performs the model-based segmentation by a process that includes:
  determining from the patient data medical information that is separate and distinct from the medical image of the patient;
  determining a predicted appearance of the anatomical structure in the medical image based on the medical information; and
  adjusting or setting a segmentation parameter based on the medical information so as to adjust the model-based segmentation to be consistent with the predicted appearance of the anatomical structure in the medical image, the segmentation parameter being a parameter of at least one of the deformable model and the adaptation technique.

16. The medium of claim 15, wherein the segmentation parameter has a pre-initialization value for use in adapting the deformable model to a reference appearance of the anatomical structure, and wherein the program causes the processor to:
  determine, based on the medical information, a deviation of the predicted appearance of the anatomical structure from the reference appearance; and
  adjust or set the segmentation parameter to accommodate the deviation.

* * * * *